United States Patent [19]

Libit

[11] 3,993,664
[45] Nov. 23, 1976

[54] PREPARATION OF PROSTAGLANDIN INTERMEDIATES

[76] Inventor: Lawrence Libit, 639 Library Place, Evanston, Ill. 60201

[22] Filed: June 24, 1974

[21] Appl. No.: 482,082

[52] U.S. Cl. .................... 260/343.3 R; 204/158 R
[51] Int. Cl.² .................. B01J 1/10; C07D 307/83; C07D 309/22
[58] Field of Search .............. 260/343.3, 345.8; 204/158 R

[56] References Cited
UNITED STATES PATENTS

| | | | |
|---|---|---|---|
| 3,711,515 | 1/1973 | Kelly | 260/343.3 |
| 3,778,461 | 12/1973 | Brown et al. | 260/343.3 |
| 3,781,306 | 12/1973 | Kelly | 260/343.3 |
| 3,816,460 | 6/1974 | Kelly | 260/343.3 |
| 3,816,461 | 6/1974 | Kelly | 260/343.3 |
| 3,816,462 | 6/1974 | Kelly | 260/343.3 |
| 3,818,045 | 6/1974 | Kelly | 260/343.3 |
| 3,823,138 | 7/1974 | Rheenen | 260/343.3 |

*Primary Examiner*—Howard S. Williams
*Attorney, Agent, or Firm*—Wallenstein, Spangenberg, Hattis & Strampel

[57] ABSTRACT

Preparation of prostaglandin intermediates by reacting mono-tetrahydropyranyl ether with 3-acetoxy acryloyl chloride in the presence of pyridine to produce the 3-acetoxy acryloyl ester of said ether. The said ester is then irradiated to effect photocyclization whereby to close the ring in said ester. The resulting compound is then treated with methanol containing a small amount of potassium carbonate whereby to produce the "Corey" intermediate. Those intermediates which are novel are also claimed.

8 Claims, No Drawings

PREPARATION OF PROSTAGLANDIN INTERMEDIATES

My invention is directed to the preparation of certain intermediates which have particular use in processes for producing prostaglandins. More specifically, it is directed to a process for producing the so-called "Corey" intermediate which, as is well known, may be illustrated by the following formula

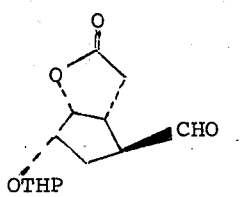

E. J. Corey et al., *J. Am. Chem. Soc.*, 93, 1490 (1971); E. J. Corey, *Ann. N.Y. Acad. Sci.*, 180, 24 (1970).

Routes to the preparation of prostaglandins starting with the Corey intermediate are well known to the art and such routes possess a number of significant advantages over various other known procedures for the preparation of prostaglandins. However, process routes heretofore known for the preparation of the Corey intermediate, starting with readily available materials, are cumbersome and time-consuming and involve a very substantial number of steps with the result that the preparation of the Corey intermediate is very costly. Furthermore, the Corey intermediate is a rather unstable product and since it cannot satisfactorily be kept for any substantial or appreciable period of time without breakdown or destruction, it is necessary to use it within a relatively short period of time after it has been prepared for the further processing thereof in the preparation of prostaglandins therefrom.

In accordance with my invention, the Corey intermediate is prepared in good yields by a process which involves only a very few steps from the starting material referred to below. Furthermore, the process can be stopped just short of the preparation of the Corey intermediate with the production of a novel product, which is an intermediate for the Corey intermediate, which aforesaid novel product has good stability over a relatively substantial period of time. The result is that said stable product can be prepared and stored or shipped as such and then readily and easily converted to the Corey intermediate at such time as it is desired to carry out the production of prostaglandins from the Corey intermediate.

My invention may be illustrated by the following reaction scheme:

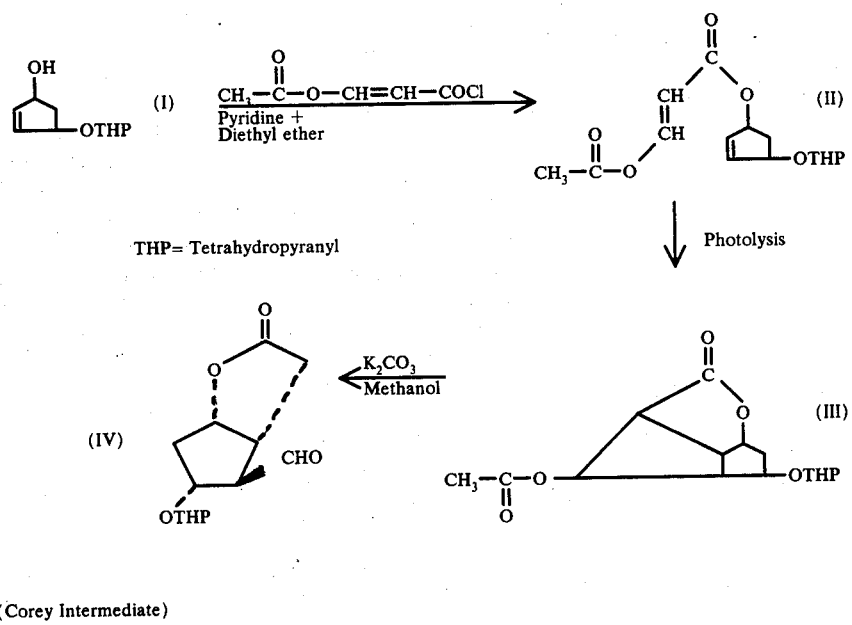

(Corey Intermediate)

Stated briefly, and as may be noted from the above, the Corey intermediate, starting with mono-tetrahydropyranyl ether, is produced by a series of steps which comprise esterifying said ether with 3-acetoxy acryloyl chloride, photolyzing said ester by irradiation to effect ring closure, and then treating said closed ring compound with methanol containing a small amount of a base, for instance, potassium carbonate whereby to produce the Corey intermediate. The several reactions, generally speaking, can be carried out in a single reactor. The starting mono-tetrahydropyranyl ether is readily produced from commercially available cyclopentene-1,4-diol, utilizing the procedure described by E. J. Corey et al., *J. Am. Chem. Soc.*, 94, 4014 (1972).

In more specific terms, an inert organic solvent solution, particularly a diethyl ether solution, of mono-tetrahydropyranyl ether, is reacted with a diethyl ether solution of 3-acetoxy acryloyl chloride in the presence of pyridine at a low temperature, for instance, −20° to +25° C., initially at about 0° C. for a number of hours, generally about 2 to 4 hours. The reaction mixture is filtered to recover the 3-acetoxy acryloyl ester of said ether and is isolated in about 60–90% yield. It may, if desired, be purified by conventional procedures. IR, NMR and mass spectral analysis are consistent with the structure of Compound (II) above. Compound (II), in the form of a solution thereof in a liquid hydrocarbon solution containing diethyl ether and, especially advantageously, a photosensitizing agent such as, for instance, acetophenone or benzophenone, is then subjected to photolysis or photocyclization to effect the ring closure reaction shown in Compound (III) above. Photocyclization is effected by irradiation with any of various sources of electromagnetic or like energy. It is convenient and desirable, however, to utilize ultraviolet irradiation. The ring closed Compound (III) is then readily converted to the Corey intermediate by treatment with methanol or ethanol containing a small amount, for instance, of 50 mg of potassium carbonate in 50 ml of the methanol or ethanol.

The following non-limiting Example is illustrative of the process of my invention.

EXAMPLE a. Preparation of Intermediate Compound (II)

A solution comprising 10 mmoles of 3-acetoxy acryloyl chloride in 100 ml of dry diethyl ether is gradually added, with agitation, to a solution made up of 10 mmoles each of the mono-tetrahydropyranyl ether and of pyridine and 10 ml of dry diethyl ether at room temperature. After standing overnight at room temperature, the reaction mass is filtered and the resulting precipitated 3-acetoxy acryloyl ester of the mono-tetrahydropyranyl ether, namely, Compound (II), is recovered in an approximately 60–90% yield.

b. Preparation of Compound (III) from Compound (II)

A solution containing 10 mmoles of Compound (II), 100 ml of hexane, 10 ml of diethyl ether and 50–500 mg of acetophenone is irradiated, in an inert gas atmosphere such as, for instance, pure argon or nitrogen, with a high pressure Hanovia Type L lamp fitted with a COREX or VYCOR filter for a period of 2 hours whereby there is obtained, in approximately 80% yield, Compound (III). Compound (III) is distinctly more stable than the Corey intermediate, produced in part (c) of this Example.

c. Conversion of Compound (III) to Compound (IV)

Compound (III), produced above, is admixed with 100 ml of methanol containing 4 mmoles of potassium carbonate and allowed to stand at room temperature for about ½ hour to 2 hours to produce Compound (IV), the heretofore known Corey intermediate, in an approximate yield of 90%. Compound (IV) is identified as the Corey intermediate by comparison with an authentic sample of the latter, using IR, NMR and mass spectral analysis. The said Compound (IV) is rather unstable. It is convertible into various prostanoids in high yields by procedures known to the art.

I claim:

1. In a process for producing intermediates useful in the production of prostaglandins, the steps which comprise:

a. providing a solution of mono-tetrahydropyranyl ether in an inert organic solvent together with pyridine,
b. admixing said solution with an inert organic solvent solution of 3-acetoxy acryloyl chloride to produce the 3-acetoxy acryloyl ester of mono-tetrahydrofuranyl ether, and
c. then subjecting said ester to photocyclization to effect ring closure to produce a compound having the formula

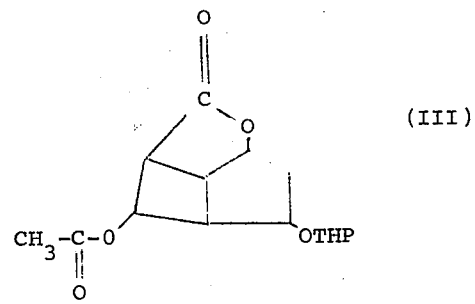

2. The process of claim 1 wherein the inert organic solvent is diethyl ether.

3. The process of claim 2, which includes the step of treating the photocyclized closed ring compound with methanol containing a small proportion of a base to produce the compound having the formula

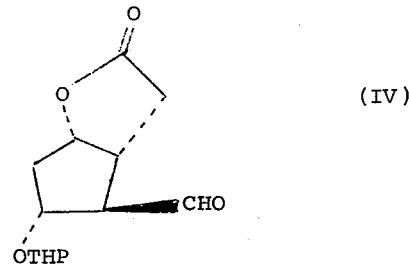

4. The process of claim 3 wherein the base is potassium carbonate.

5. The process of claim 1, which includes the step of treating the photocyclized closed ring compound with a lower alcohol containing a small proportion of a base to produce the compound having the formula

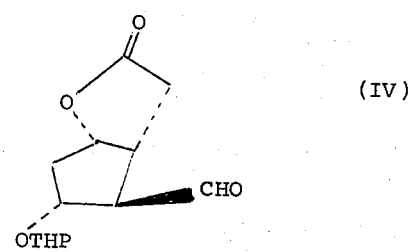

6. The process of claim 5 wherein the base is potassium carbonate.

7. Compounds, useful in the production of prostaglandins, selected from the group of those having the following formulae:
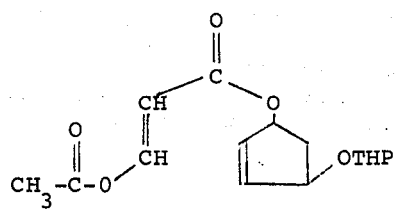
(II)
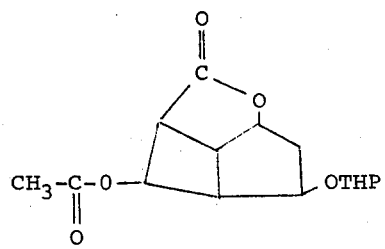
(III)
8. A compound having the formula
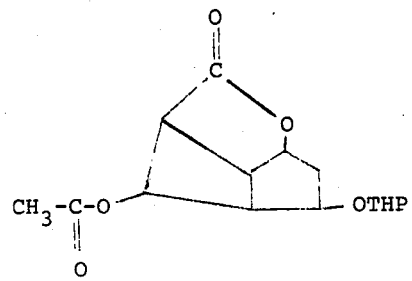
(III)
* * * * *